United States Patent [19]
Sterzer

[11] 4,190,053
[45] Feb. 26, 1980

[54] APPARATUS AND METHOD FOR HYPERTHERMIA TREATMENT

[75] Inventor: Fred Sterzer, Princeton, N.J.

[73] Assignee: RCA Corporation, New York, N.Y.

[21] Appl. No.: 808,292

[22] Filed: Jun. 20, 1977

[51] Int. Cl.² ............................................. A61N 5/02
[52] U.S. Cl. ............................. 128/399; 73/355 EM; 219/10.55 B; 219/10.55 M
[58] Field of Search ............... 128/2 H, 369, 399, 404, 128/413, 421–422, 2 A; 73/355 R, 355 EM; 219/10.55 B, 10.55 M, 10.55 F, 10.55 M

[56] References Cited

U.S. PATENT DOCUMENTS

| | | | |
|---|---|---|---|
| 2,407,690 | 9/1946 | Southworth | 128/422 |
| 2,848,626 | 8/1958 | Brackmann | 73/355 R |
| 3,451,254 | 6/1969 | Maley | 73/355 EM |
| 3,893,111 | 7/1975 | Cotter | 128/2 H |
| 4,002,175 | 1/1977 | Brainard et al. | 128/399 |
| 4,016,886 | 4/1977 | Doss et al. | 128/422 |
| 4,049,938 | 9/1977 | Ueno | 73/355 EM |

FOREIGN PATENT DOCUMENTS

| | | | |
|---|---|---|---|
| 149914 | 12/1961 | U.S.S.R. | 73/355 R |
| 149914 | 7/1962 | U.S.S.R. | 73/355 R |

OTHER PUBLICATIONS

Gunn, S. A. et al. "Effects of Microwave Radiation on the Male Endocrine System".
Ely, T. S. et al., "Heating Characteristics of Laboratory Animals Exposed to Ten Centimeter Microwaves", IEEE Trans BME, Oct. 1964, pp. 123–137.
Guy, A. W. et al., "Determination of Power Absorption in Man Exposed to HF EM Fields by Thermographic Measurements on Scale Models" IEEE Biomed Engr. Trans., Sep. 1976, vol. BME-23, No. 5, pp. 301–371.
Davis, George R. "Microwaves Score TKO in Fight Against Cancer", Microwaves, Oct. 1976, pp. 14, 16.
Zimmer, R. P. et al., "Selective EM Heating of Tumors in Animals in Deep Hypothermia", IEEE Trans. on Microwave Theory & Techniques vol. MTT-19, #pp. 238–245, Feb. 1974.
Barrett, A. H. et al., "Sub-Cutaneous Temperatures: A Method of Non-Invasive Sensing", Science vol. 190, 11/14/75 pp. 669–671.

*Primary Examiner*—Robert W. Michell
*Assistant Examiner*—Frank J. Jaworski
*Attorney, Agent, or Firm*—H. Christoffersen; Joseph D. Lazar; Robert L. Troike

[57] ABSTRACT

The apparatus and method provides accurate temperature measurement and control of living tissue during hyperthermia treatment. The temperature is measured by a radiometer tuned to the frequency bandwidth of an energy source providing energy for heating living tissue. The radiometer measures essentially the radiant energy and thereby the temperature of the same volume of living tissue that is heated by the source during the hyperthermia treatment.

10 Claims, 7 Drawing Figures

APPARATUS AND METHOD FOR HYPERTHERMIA TREATMENT

CROSS REFERENCE TO RELATED APPLICATIONS

Of interest are the following U.S. patent applications: Ser. No. 715,220, filed on Aug. 18, 1976 and Ser. No. 671,554, filed on Mar. 29, 1976, now abandoned, both assigned to the same assignee as the present application.

BACKGROUND OF THE INVENTION

1. Field of the Invention

This invention relates to an apparatus and method providing hyperthermia treatment of living tissue and more particularly to an accurate measurement and control of the temperature of the living tissue during hyperthermia treatment.

2. Description of the Prior Art

When a patient has a cancerous tumor, a surgical procedure is often employed to remove the tumor. However, in certain circumstances the use of surgical procedures may not be advisable.

Since ancient times, medical practitioners have known that the patient may be successfully treated by raising the temperature of a tumor, a treatment generally referred to as hyperthermia. One method of hyperthermia is the elevation of the temperature of a large portion of the patient's body where the tumor is located. Accordingly, in the late 1960's, medical practitioners treated patients with tumors in their arms and legs by a perfusion therethrough of hot blood. In another method, patients with tumors in their bladders were treated by flushing the bladders with hot fluid. In 1974 Scottish medical practitioners immersed patients in hot wax. Other medical practitioners have elevated the body temperature of patients by infecting the patients with malaria.

It is known that certain tumors either shrink or disappear at a temperature of approximately 43° C. Based on this knowledge, one preferred method of hyperthermia tumor treatment provides for heating the tumor to that temperature by heating only so much of the tissue as includes the tumor. Medical practitioners have used microwave radiation energy to elevate the temperature of the so-called "local tissue" which is contiguous and closely adjacent to the tumor. Depth of penetration of the energy signal into the tissue of the body is a well-known and well-behaved function of the signal frequency employed. The temperature of the tissue is directly dependent on the power or intensity of the microwave energy applied to the surface of the body tissue. The volume of the tissue to be heated can be controlled by the electrical and geometric design of the microwave applicator. The microwave radiation may be controlled to elevate rapidly the temperature of a known volume of tissue that extends from the surface of the skin to a known depth beneath the skin. During microwave radiation, it is desirable to prevent over-heating of the tumor as well as surrounding living tissue. Therefore, it is correspondingly desirable to provide an accurate measurement of the temperature of the living tissue particularly at the site of the tumor. Prior methods of hyperthermia treatment employed thermocouples to measure the temperature of the tissue. Thermocouples are either attached to the surface of the skin or invasively positioned beneath the skin. The thermocouple while measuring temperature during treatment can be used to switch-off the microwave irradiation to the tissue upon sensing a predetermined temperature. However, thermocouples can only measure the temperature of the tissue at the point of contact. Thus, thermocouples for hyperthermia treatment are located at the skin surface or subcutaneously by being positioned invasively at the site of the tumor, requiring thereby surgical insertion of the thermocouple. Also, thermocouples, being metallic, distort the applied microwave field and induce extraneous heating effects which contribute to inaccurate temperature measurements. Furthermore, thermocouples behave as radiation detectors and therefore are susceptible to pick-up signals of radiated frequencies other than from the applied microwave source, whereby inaccurate temperature readings may occur. It appears, thus, that the use of thermocouples for measurement of temperature does not provide the accuracy required for improving the results of hyperthermia treatments.

It is also known to use radiometers to sense subcutaneous temperatures for diagnosing malignant tumors. For further information of this technique see an article in Science, Nov. 14 1975, Volume 190, pages 669–671, by Barrett and Meyers entitled "Subcutaneous Temperature: A Method of Noninvasive Sensing." Also see an article in The Review of Scientific Instruments, July 1946, Vol. 17, No. 7, pages 268–275, by R. H. Dicke, entitled "The Measurement of Thermal Radiation at Microwave Frequencies."

There is a need in hyperthermia treatment of living tissue, whether or not tumors are included therein, to provide an accurate measurement of the volume of the heated tissue to minimize if not eliminate the risk to the patient for successful hyperthermia treatment.

SUMMARY OF THE INVENTION

According to this invention, hyperthermia treatment of living tissue is provided by irradiating tissue with energy signals at a selected frequency and intensity and detecting from the radiated living tissue radiant energy at the selected frequency.

DESCRIPTION OF THE PREFERRED EMBODIMENT

Figure 1:
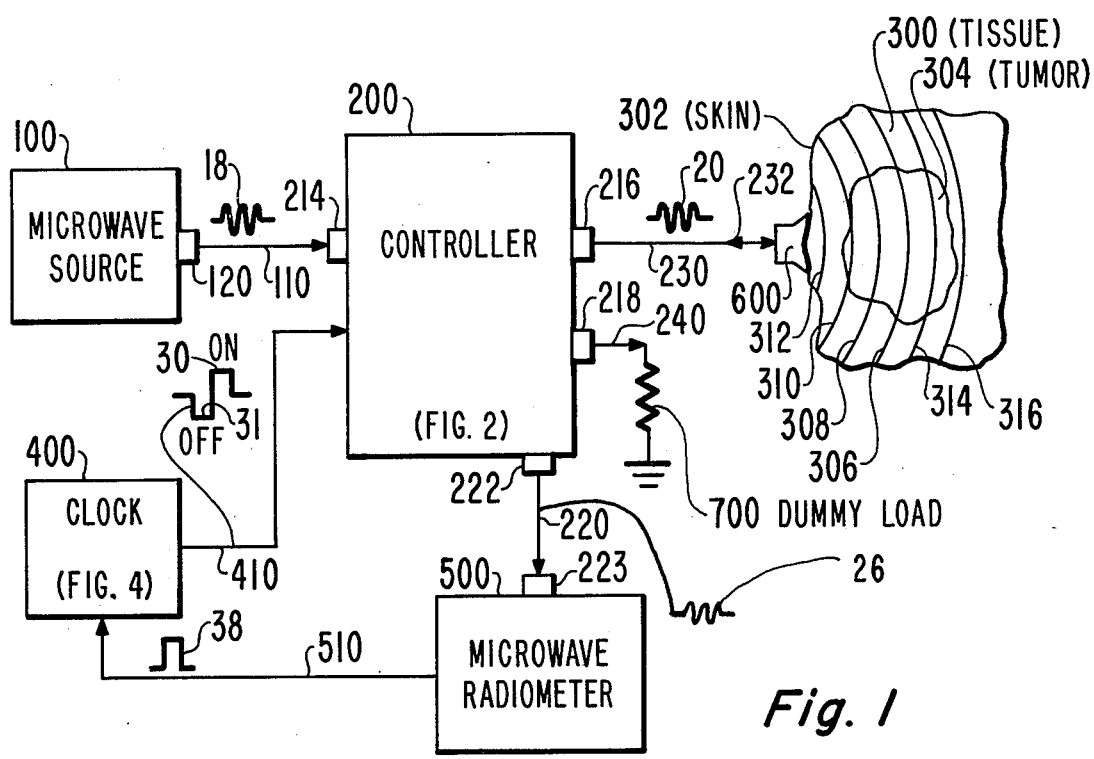
FIG. 1 is a block schematic of the preferred embodiment of the invention.

FIG. 1 illustrates the arrangement and organization of the main components of the preferred embodiment of the invention. The hyperthermia apparatus comprises a microwave source 100 providing a microwave signal 18 coupled through connectors 120 and 214 to a controller 200 which provides a microwave signal 20 via connector 216 to applicator 600 for irradiating tissue 300 at timed intervals under control of a clock 400. The irradiating signal 26 20 is interruped to allow the tissue 300 to radiate a signal (in the direction of arrow head 232) for measurement by a microwave radiometer 500 coupled to controller 200 via conductor 220 and connectors 222 and 223.

Source 100 is a known tunable microwave signal generator capable of providing radio frequency signals in the frequency spectrum of 900 to 10,000 megahertz, at signal power levels in the order of 1.0 to 100 watts. Source 100 is adjusted to provide a signal at terminal 120 at a predetermined frequency to effect the desired depth of penetration into the body tissue and at a predetermined power level for the desired heating of the living tissue as indicated above.

Reference is made to an article of Herman P. Schwan, entitled "Interaction of Microwave and Radio Frequency Radiation with Biological Systems," published in the IEEE Transactions on Microwave Theory and Techniques, Volume MTT-19, No. 2, February 1971, for information concerning microwave heating effects on biological systems.

Controller 200 routes the microwave signal via input microwave path 110 and output terminal 216 to the applicator 600. A suitable clock 400 and controller 200 are illustrated respectively in FIGS. 4 and 2 to be described.

Applicator 600 is a suitable microwave waveguide for coupling the microwave signal 20 to the body tissue 300. Applicator 600 is filled with a dielectric material having a dielectric constant that substantially equals the dielectric constant of the living tissue 300. Typically, the dielectric constant of the applicator material and the tissue 300 is in a range of 5 to 50. The input to applicator 600 is connected to controller 200 through a 50 ohm coaxial line 230 and connector 216 of any suitable type. Applicator 600 substantially matches the impedance of the connector 216 to the impedance of the tissue 300. Applicator 600 may be of the type of applicator that is the subject of U.S. Pat. Applications, Ser. No. 715,220, filed on Aug. 18, 1976, and Ser. No. 671,554, filed on Mar. 29, 1976, (now abandoned), both assigned to RCA Corporation, the assignee of the instant application. Applicator 600 may be of any suitable shape. Furthermore, the applicator 600 may be in the form of a coaxial type that may be filled with dielectric material Microwave radiometer 500 is of a suitable known type that measures radiant energy (signal 26) and is preferably tunable to a selected band of frequencies in the microwave range, more particularly, in the frequency range of the microwave signal 18. Radiometer 500 is suitably calibrated or otherwise arranged to provide in response to signal 26 a signal representing the average temperature of the heat energy measured. Radiometer 500 is further provided with a sensor circuit (not shown) that operates in response to the radiometer signal representing the average temperature of the measured heat energy to generate a temperature control signal 38 over its output path 510 to maintain a predetermined average temperature range (e.g., 43.0°±0.5° C.) of the tissue 300. The measured radiant energy signal 26 is applied to radiometer 500 via connector 223. The sensor circuit of radiometer 500 generates signal 38, more particularly, the leading edge transistion 38a (FIG. 3), when the temperature of the radiant energy senses by radiometer 500 is approximately 43.5° C. and continues until the temperature drops to approximately 42.5° C., causing signal 38 to return to zero at the trailing edge 38b, as indicated in FIG. 3.

Clock 400 provides timed control signals 31 which define the "off" time period to apply microwave signal 20 from source 100 to the tissue 300 and for the microwave signal 20 to be absorbed by the living tissue 300, and the "on" time period 30 for microwave radiometer 500 to measure the irradiant energy signal 26 of the heated tissue 300. Signal 38 coupled to clock 400 causes controller 200 to continue the connections of the energizing signal 20 from applicator 600 to dummy load 700 and the radiometer 500 measuring the radiated energy signal 26 from the tissue 300. Dummy load 700 has an impedance value equal to the characteristic impedance of microwave source 100 and thus provides a termination for power absorption of microwave source 100 when the microwave source 100 is not coupled to tissue 300. Without being exposed to the energizing signal 20, the tissue temperature will drop. When the tissue reaches approximately 42.5° C. as sensed by the radiometer 500, signal 38 returns to zero to thereby switch signal 20 back on to energize the tissue 300 via applicator 600 and simultaneously disconnect radiometer 500 from signal path 230 to prevent it from damage by the higher energy level of signal 20.

Figure 2:
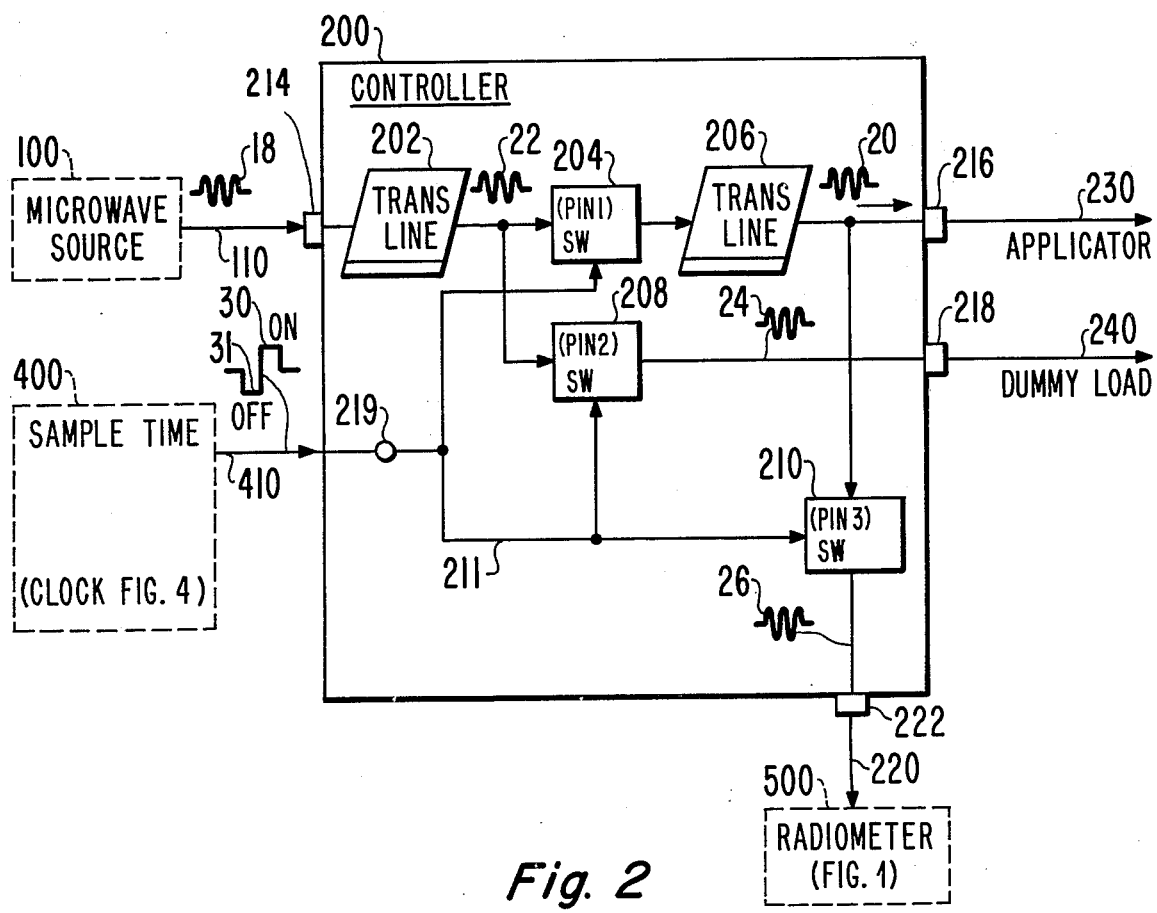
FIG. 2 is a detailed schematic of the controller of FIG. 1.
Figure 3:
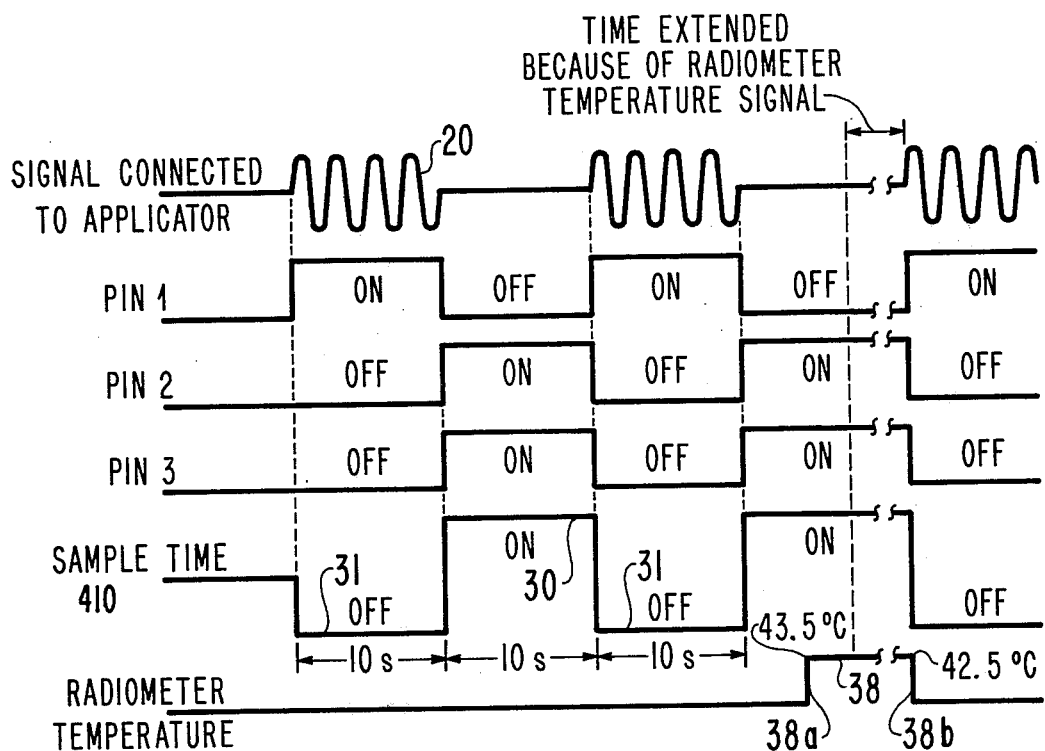
FIG. 3 illustrates waveforms used by or generated within the controller.

Reference is now made to FIGS. 2 and 3 illustrating a suitable controller 200 and waveforms associated therewith. The input path 110 from microwave source 100, and output paths 230, 240, and 220 to applicator 600, dummy load 700, and radiometer 500, respectively, are suitably controlled by switches 204, 208 and 210. The switches 204, 208 and 210 are preferably formed of PIN diodes (PIN 1, PIN 2, PIN 3) arranged with a suitable bias control shown functionally as a bias bus 211 via clock 400 to perform the on-off switching function required, as well known in the art. Any other suitable microwave switches capable of handling the energy signals (18, 22, 20, etc.) may be used.

Transmission lines 202 and 206 are provided to conduct the microwave energy signal 18 to source 100 to applicator 600. Lines 202 and 206 that may be used in practice of the present invention may be of any suitable form including coaxial cables, waveguides or strip transmission lines.

Figure 4:
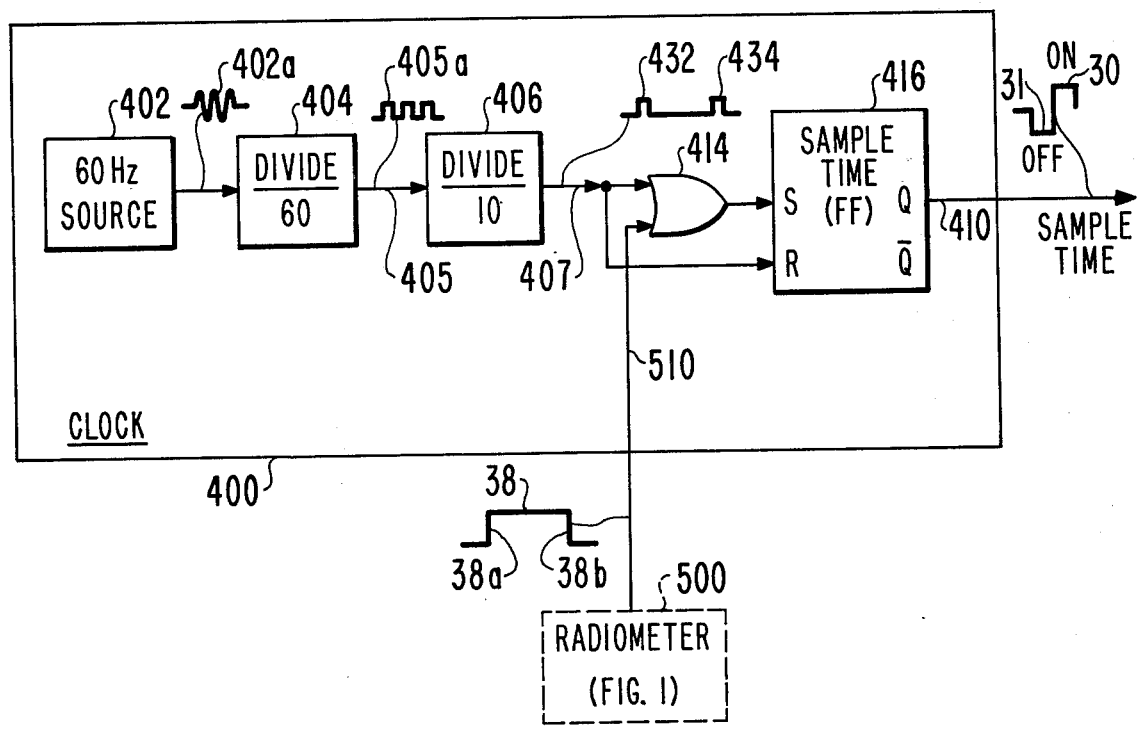
FIG. 4 is a detailed schematic of the clock of FIG. 1.

PIN1 204, is turned "ON" (conduct) and "OFF" (non-conductive) by negative and positive clock voltages 31 and 30 to be described with FIG. 4. Concurrently, PIN2 208, and PIN3 210 are turned "OFF" (non-conduct) and "ON" (conduct) by negative and positive voltages 31 and 30, via bus 410, terminal 219 and bus 211.

PIN1 204 when turned "ON" connects transmission line 202 to transmission line 206 allowing the r.f. signal 18 to be coupled to applicator 600 via path 230. PIN2 208 when "ON" couples transmission line 202 to the dummy resistor load 700 via path 240 and coupler 218 to thereby transfer the source signal (18) from the applicator (600) for power absorption by dummy load 700 during the time the applicator is not energized as will be described.

Figure 5:
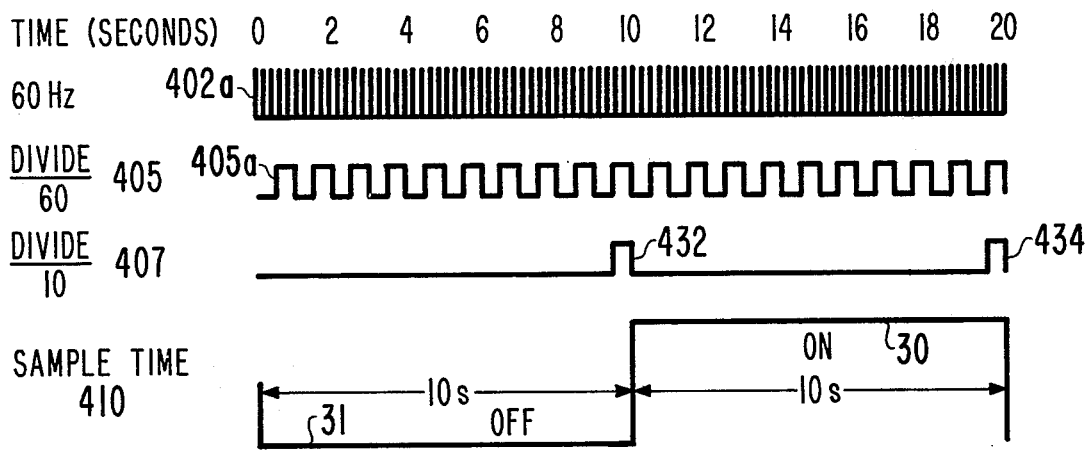
FIG. 5 is a timing diagram of the clock signals of FIG. 4.

FIGS. 4 and 5 illustrate a suitable clock 400 for controller 200 and a timing diagram of clock signals, respectively. It should be understood that there are many suitable clock implementations possible dependent upon the timing involved in a particular hyperthermia treatment, and FIG. 4 exemplifies only one such example.

Reference is now made to FIG. 4. The reference time source for clock 400 is a 60 Hz source 402. The output 402a of source 402 is counted down by a divide-by-60 circuit 404 to develop a one Hz signal 405a. The one Hz signal is applied to a divide-by-ten circuit 406 to develop a one pulse per ten second signal 432 on path 407.

In the following discussion, it is assumed that any signal, such as 432, present on 407 is applied simultaneously to both the set and reset inputs of a suitable flip-flop 416. It is further assumed that flip-flop 416 responds to any signal, such as 432 by changing states, i.e., from its set to reset, and vice versa. Signal 432 is inputted into an OR circuit 414 and then to sample time (set-reset) flip-flop 416. The radiometer temperature signal 38 from radiometer 500 is connected to OR circuit 414 over path 510.

FIG. 5 shows the various signals that are related to the clock circuit as will be described further hereinafter. The timing signals involved in the development of the control signals (30, 31) are divide-by-sixty (405a) and divide-by-ten 432. Sample time 410 comprising signals 31 and 30, for example, have durations of 10 seconds in the "OFF" state and 10 seconds in the "ON" state for a total period of 20 seconds as seen by the time scale at the top of FIG. 5. Upon the occurrence of the first divide-by-ten pulse 432, sample time signal 30 starts over path 410. Signal 30 remains in this condition until the next divide-by-ten pulse 434, causing FF 416 to be reset, producing the sample time signal 31 over path 410. The next (third) divide-by-ten pulse (not shown) repeats the cycle. Thus, the signals 432, 434 define a 20 second period for energizing the tissue 300 for a 10 second portion thereof. However, the tissue temperature is regulated to a predetermined value by altering the time during which the applicator is energized in response to the radiometer temperature signal 38.

The operation of PIN1 204, PIN2 208, and PIN3 210 as used in controller 200 (FIG. 2) will now be described by referring to FIG. 3. FIG. 3 shows the timing of the controller 200 and the hyperthermia operations being performed. Assuming the initial conditions are that sample time signal 31 is at a negative voltage, allowing PIN1 to be turned "ON", connecting the microwave source (100) to applicator (600). Concurrently, PIN2 and PIN3 are turned "OFF", providing an open circuit to the microwave radiometer 500 and dummy load 700. At the predetermined sample time (10 seconds) the sample time signal changes to a positive voltage (30) causing PIN2 and PIN3 to be turned "ON" and PIN1 to be turned "OFF". During this time (30), signal 20 is removed (PIN1 "OFF") from applicator 600 and applied (PIN2 "ON") to the dummy load 700, and PIN3 being "ON", connects radiometer 500 to applicator 600. Radiometer 500 now measures the radiant energy via signal 26 (FIG. 2) from the volume of irradiated (heated) tissue 300.

More specifically, one cycle of the sample time signal 410 (FIG. 3) causes signal 20 to be applied to applicator 600 for 10 seconds during negative portion 31 and, for the next 10 seconds positive portion 30 causes the signal 20 from applicator 600 to be removed and connects the microwave radiometer 500 to the applicator 600, allowing measurement of the radiant energy via signal 26 from the heated tissues 300. The measurement continues for 10 seconds during the positive signal 30 and then terminates upon the occurrence of negative signal 31. Source 100 is reconnected to applicator 600 via signal 20 for 10 seconds during negative signal 31. Then signal 30 becomes a positive voltage to repeat the cycle. If during the time when radiometer 500 is measuring the radiant energy via signal 26 from the volume of heated tissue 300, the temperature reaches approximately 43.5° C., signal 38 from radiometer 500 is applied to clock 400, holding thereby signal 30 in a positive voltage condition (FIG. 3) until the temperature reduces to approximately 42.5° C., whereby signal 31 becomes a negative voltage in response to signal 38 returning to zero at transition 38b to reapply thereby signal 20 to applicator 600.

According to the invention, the microwave radiometer (500) provides an average temperature measurement of the radiant energy of the volume of microwave energy heated tissue (300).

More particularly, this average temperature value is determined by tuning the radiometer to receive radiant energy signal 26 radiated from the heated tissue 300 via applicator 600 and transmission line 220 at a frequency, or band of frequencies, corresponding to the frequency (or band of frequencies) of the excitation signal 18. Since the effective depth of penetration of the microwave signal coupled from the applicator 600 into the tissue 300 is dependent on the frequency of the signal, while the average temperature of the heated volume of tissue is dependent on the power level or intensity of the microwave signal 20, radiometer 500 when turned to the same frequency or band of frequencies as that of the excitation signal will sense radiant energy and thus the temperature of the tissue that are essentially related only to the heating effect caused by the energizing signal. By so tuning the radiometer, radiated energy related to the heat energy of other frequencies in the spectrum inherently existing in the thermal energy of the tissue 300 will not be sensed and thus will not affect and thereby distort the desired temperature measurement. It should thus be appreciated that by measuring the energy and thus the temperature of the tissue 300 that has been heated by the microwave source signal only it is possible to control the temperature of the tissue quite accurately, within the range or performance capability of the microwave source 100 and the radiometer 500. In practice, a radiometer may be calibrated to provide temperature indications in steps in the order of 0.1° C. As indicated above, it is known that a malignant tumor (304) may be therapeutically treated to cause a remission of its malignancy by heating it at a temperature of 43.5° C.±0.5° C.

Thus, when signal 20 is coupled to applicator 600 to heat the volume of tissue 300, signal 20 will penetrate the tissue a depth that depends on the nature of the tissue being irradiated (fat, muscles, bones, normal tissue or atrophied tissue, etc.) and on the frequency of the microwave signal 20. After the signal 20 has been interrupted in its radiation of the volume of tissue, radiometer 500 is coupled to the applicator to measure the radiant energy signal 26 radiated by the tissue 300. The frequency of the radiant energy preferably selected for the measurement of the temperature of the tissue according to the invention is the frequency of the applied microwave source and the radiometer tuned to that frequency will measure essentially only the radiant energy of the heated volume at that frequency. This radiant energy is radiated from the volume of tissue 300 that absorbed the irradiating microwave signal 20, and the measured temperature will be the average temperature of this volume. This measurement of the average temperature of the volume of the tissue, it will now be appreciated, overcomes the problem of prior hyperthermia treatments employing externally or invasively positioned thermocouples for temperature measurement as discussed herein before in the "Prior Art" section of this specification.

In practice, the subcutaneous depth of penetration for effectively heating the tissue and, more importantly, the tumor that is embedded in the tissue, is determined by the physical location of the subcutaneous tissue and tumor. The frequency of the irradiating signal determines the effective depth of heating penetration. At present, in accordance with FCC (Federal Communication Commission) regulations certain frequencies 915±13 MHz and 2,450±50 MHz, for example, are available for hyperthermia equipment. These frequencies may be utilized to implement the present invention. It should be understood, nevertheless, that other signal frequencies may be used, subject to governmental regulations, that are in general included within the frequency spectrum that comprises black body radiation. Accordingly, the invention may be practiced with radiating signals as high as 3 GHz for relatively shallow subcutaneous tissue and 0.9 GHz for deeper tissue.

Figure 6A:
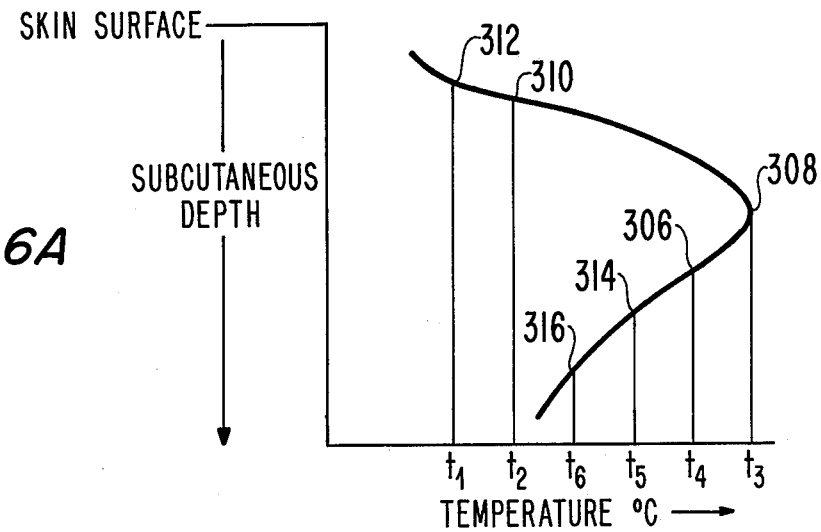
FIGS. 6A and 6B are schematics of the temperature profile of a volume of tissue.
Figure 6B:
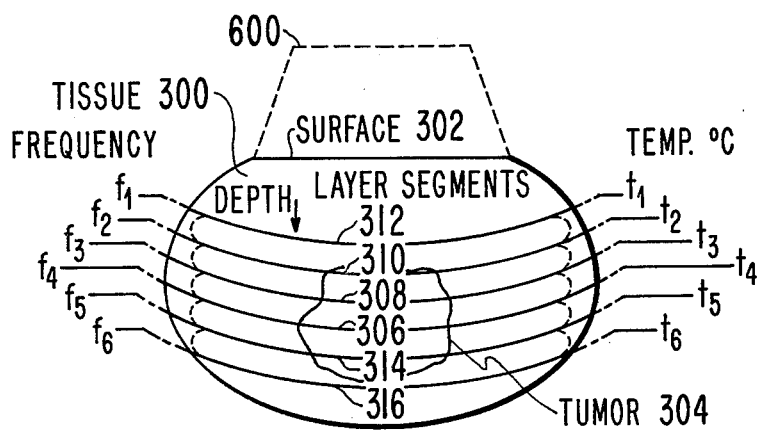

In the practice of the invention, a temperature gradient will be developed throughout the mass of tissue that is exposed to the radiation received through the applicator in a direction generally normal to the surface of the skin. The gradient is dependent on the frequency and intensity of the radiating signal. FIGS. 6A and 6B illustrate a temperature gradient that may be developed during a hyperthermia treatment.

Assume that the irradiation signal (20) heats the tissue 300 and the tumor 304 to a temperature t4 along a temperature contour line 306 (FIGS. 1 and 6B). It is known that heated tissue will have an energy state that will exhibit a frequency spectrum corresponding to the temperature of the respective depths of the volume of tissue independent of the means by which the energy was added to the system. Accordingly, a temperature vs depth profile of the volume of tissue comprising the tumor 304 can be developed by tuning radiometer 500 in steps scanning the frequencies above and below the excitation frequency f4 of signal 20.

Radiometer 500 is coupled into the circuit to read or to measure the radiant energy from the tissue 300 and tumor 304 at several different frequencies above and below frequency f4. Thus, if the radiometer is adjusted to measure radiant energy at a frequency f3 (higher than f4), the average temperature corresponding to that depth within the volume of tissue 300 may be represented by the temperature contour line 308. Similarly, at a frequency f2 which is higher than f3 and thus f4 another temperature t2 will be manifested along equal temperature contour line 310 and also line 312 for a still higher frequency f1. In a similar manner as the radiometer is tuned to lower frequencies, the temperature contour lines represent an average temperature of depths within tissue 300 that are deeper from the skin surface than temperature contour line 306 manifesting t4, the lower depth scanning is achieved by tuning the radiometer at a frequency of f5 for a contour line 314 which is lower than f4 to obtain temperature t5, while line 316 represents a contour for a temperature t6 by tuning the radiometer at a frequency of f6 which is lower than f5 and thus f4. A profile of this temperature gradient is shown in FIG. 6A along the contour temperature lines 312, 310, 308, 306, 314, and 316. The corresponding depth of each equal temperature line is indicated by the abscissa. Typical frequencies are 2450 MHz for f4 with steps of 100 MHz, for example, for each increment above and below f4. Typical temperatures may be 43.0° C. for f4 with steps of 0.1° C. above and below that temperature. Accordingly, in the practice of the invention, the effect of heating the tumor 304 may be appraised to determine which portions of the tumor are being heated to the critical therapeautic temperature range of 43.0°±0.5° C.

It is of significant importance that the hyperthermia apparatus of this invention may be used to treat tissues infected with malignant tumors by controlling the temperature of the tumor to a temperature of 43°±0.5° C., the temperature range which has been recently identified to be critically related to effect the remission of a malignant tumor. Furthermore, the apparatus may be used for hyperthermia treatment for other purposes such as therapeutic heating of the body organs such as the heart, liver, kidneys, pituitary glands, etc.

What is claimed is:

1. Apparatus for heating living tissue with microwave signals and detecting radiant energy from that tissue comprising:
    a. source means for providing irradiating microwave signals at a selected frequency and intensity;
    b. means for coupling said microwave signals to irradiate said living tissue to thereby increase the heat energy and thereby the temperature of said tissue;
    c. means to interrupt the coupling of said signals to said tissue; and
    d. detecting means coupled to said tissue to detect radiant energy related to said frequency from said tissue only when said microwave irradiation signals to said tissue are interrupted, said radiant energy being indicative of the temperature of said tissue.

2. Apparatus according to claim 1 wherein said detecting means comprises a radiometer tuned to said selected source means frequency.

3. Apparatus according to claim 2 wherein said radiometer includes means for generating in response to radiant energy from said tissue a signal representing a predetermined temperature indicative of the radiated heat energy from said tissue.

4. Apparatus according to claim 3 further including timing means responsive to said temperature signal for generating a first timing signal for interrupting said irradiating microwave signals when the temperature of said tissue is equal to said predetermined temperature, and for generating a second timing signal for coupling said microwave signal to irradiate said tissue when the temperature of said tissue is at a second predetermined temperature below said first predetermined temperature.

5. Apparatus according to claim 1 wherein said detecting means comprises a radiometer tuned to a frequency different from said selected source means frequency to determine thereby a temperature gradient within said tissue.

6. A method for heating living tissue with microwave signals and detecting radiant energy from that tissue comprising the steps of:
    a. generating irradiating microwave signals at a selected frequency and intensity;
    b. coupling said microwave signals to irradiate said tissue to thereby increase the heat energy and thereby the temperature of said tissue;
    c. automatically interrupting the coupling of said signals to said tissue; and
    d. automatically detecting the radiant energy related to said frequency from said tissue when said microwave irradiation signals to said tissue are interrupted, said radiant energy being indicative of the temperature of said tissue.

7. A method as set forth in claim 6 wherein said detecting step includes tuning a radiometer to said selected source frequency.

8. A method as set forth in claim 7 wherein said detecting step further includes generating in response to radiant energy from said tissue a signal representing a predetermined temperature indicative of the radiated heat energy from said tissue.

9. A method as set forth in claim 8 further including responding to said temperature signal by generating a first timing signal for interrupting said irradiating microwave signals when the temperature of said tissue is equal to said predetermined temperature, and generating a second timing signal for coupling said microwave signal to irradiate said tissue when the temperature of said tissue is at a second predetermined temperature below said first predetermined temperature.

10. A method as set forth in claim 6 wherein detecting step includes tuning a radiometer to a frequency different from said selected frequency to determine thereby a temperature gradient within said tissue.

* * * * *

UNITED STATES PATENT AND TRADEMARK OFFICE
CERTIFICATE OF CORRECTION

PATENT NO. : 4,190,053

DATED : February 26, 1980

INVENTOR(S): Fred Sterzer

It is certified that error appears in the above-identified patent and that said Letters Patent is hereby corrected as shown below:

Column 2, line 67, delete "26"

Column 2, line 68, after "signal" insert --26--.

Column 5, line 27, after "However," insert --as shown in Figure 3, to be described,--.

Column 6, line 21, change "turned" to --tuned--.

Column 6, line 46, after "tissue" insert --to--.

Column 7, line 56, delete "for" and insert --which is lower than f4 to obtain--.

Column 7, lines 56 and 57, delete "which is lower than f4 to obtain and insert --for--.

Signed and Sealed this

Twenty-eighth Day of October 1980

[SEAL]

Attest:

SIDNEY A. DIAMOND

Attesting Officer

Commissioner of Patents and Trademarks